United States Patent
Lübbe et al.

(10) Patent No.: US 10,299,997 B2
(45) Date of Patent: May 28, 2019

(54) PARTICULARLY STORAGE-STABLE AND THIXOTROPICALLY STABLE PROPHYLAXIS PASTE FOR PROFESSIONAL DENTAL USE

(71) Applicant: VOCO GmbH, Cuxhaven (DE)

(72) Inventors: Gerrit Lübbe, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 0 days.

(21) Appl. No.: 14/202,489

(22) Filed: Mar. 10, 2014

(65) Prior Publication Data

US 2014/0255490 A1   Sep. 11, 2014

(30) Foreign Application Priority Data

Mar. 11, 2013   (DE) ........................ 10 2013 004 088

(51) Int. Cl.
| | | |
|---|---|---|
| *A61K 8/24* | (2006.01) | |
| *A61Q 11/00* | (2006.01) | |
| *A61C 17/00* | (2006.01) | |
| *A61K 8/21* | (2006.01) | |
| *A61K 33/06* | (2006.01) | |
| *A61K 8/41* | (2006.01) | |
| *A61K 8/96* | (2006.01) | |
| *A61K 8/34* | (2006.01) | |
| *A61K 8/37* | (2006.01) | |
| *A61K 8/44* | (2006.01) | |
| *A61K 8/73* | (2006.01) | |

(52) U.S. Cl.
CPC .............. *A61K 8/24* (2013.01); *A61C 17/005* (2013.01); *A61K 8/21* (2013.01); *A61K 8/345* (2013.01); *A61K 8/37* (2013.01); *A61K 8/416* (2013.01); *A61K 8/442* (2013.01); *A61K 8/731* (2013.01); *A61K 8/965* (2013.01); *A61Q 11/00* (2013.01); *A61K 2800/48* (2013.01)

(58) Field of Classification Search
CPC .......... A61Q 11/00; A61K 8/00; A61K 8/898; A61K 8/24; A61K 33/06
See application file for complete search history.

(56) References Cited

U.S. PATENT DOCUMENTS

| | | | | |
|---|---|---|---|---|
| 4,976,954 A | * | 12/1990 | Kleber .................... | A61K 8/26 424/464 |
| 5,028,412 A | * | 7/1991 | Putt ......................... | A61K 8/26 424/440 |
| 6,280,707 B1 | | 8/2001 | Peterson et al. | |
| 6,303,104 B1 | * | 10/2001 | Winston ................... | A61K 8/19 424/49 |
| 7,332,150 B2 | | 2/2008 | Silber et al. | |
| 2002/0098156 A1 | | 7/2002 | Milliron | |
| 2010/0135921 A1 | | 6/2010 | Hughes et al. | |
| 2010/0135925 A1 | | 6/2010 | Haught et al. | |
| 2011/0008270 A1 | | 1/2011 | Schmid et al. | |
| 2011/0059420 A1 | | 3/2011 | Peterson | |
| 2011/0268672 A1 | | 11/2011 | Monzyk et al. | |
| 2012/0067748 A1 | * | 3/2012 | Jung ..................... | A61C 19/06 206/63.5 |

FOREIGN PATENT DOCUMENTS

| | | |
|---|---|---|
| DE | 69204942 T2 | 2/1996 |
| DE | 60210674 T2 | 4/2007 |
| DE | 60035344 T2 | 2/2008 |
| EP | 0040938 A2 | 12/1981 |
| EP | 0268763 B1 | 8/1992 |
| EP | 1278506 B1 | 1/2003 |
| EP | 1051962 B1 | 7/2007 |
| EP | 1938786 B1 | 3/2010 |
| EP | 2198836 A1 | 6/2010 |
| EP | 2286786 A1 | 2/2011 |
| WO | 1996009033 A1 | 3/1996 |
| WO | 2000059460 A1 | 10/2000 |

(Continued)

OTHER PUBLICATIONS

Online Medical Dictionary, definition of "Calcium Phosphates," printed Mar. 9, 2016 found at (http://www.online-medical-dictionary.org/definitions-c/calcium-phosphates.html), 1 page.
English Translation of German wiki page for Disodium hydrogen phosphate: https://de.wikipedia.org/wiki/Dinatriumhydrogenphosphat; accessed on Sep. 26, 2016.
European Search Report for Application No. EP14000719, dated Nov. 18, 2014.
German Search Report for Application No. DE102013004088.4, dated Sep. 4, 2013.

*Primary Examiner* — Lezah Roberts
(74) *Attorney, Agent, or Firm* — Armstrong Teasdale LLP

(57) ABSTRACT

The invention relates to a particularly storage-stable and thixotropically stable dental prophylaxis paste for professional tooth cleaning which is very easy to use and thoroughly cleans and polishes the teeth of the patient and causes little abrasion of natural tooth substance. Such a dental prophylaxis paste may comprise:

a.) a base component comprising water and humectant, b.) a cleaning body comprising a compound based on calcium phosphate in combination with pumice, c.) a buffer component, d.) a component for controlling the rheology, e.) an additive component selected from the group consisting of stabilizers, dyes, pigments and fluoridation agents, and, as wetting agent, f.) has exclusively one or more amphoteric surfactant(s), where the buffer component c.) is based on hydrogen phosphate and keeps the pH of the prophylaxis paste, measured in a 10% suspension (w/w) of the paste in water against a pH electrode, between 7 and 8.

15 Claims, No Drawings

(56) References Cited

FOREIGN PATENT DOCUMENTS

| | | | |
|---|---|---|---|
| WO | 0078270 | A1 | 12/2000 |
| WO | 2005027863 | A1 | 3/2005 |
| WO | 2009140577 | A1 | 11/2009 |
| WO | 2010009133 | A2 | 1/2010 |
| WO | 2011073194 | A2 | 6/2011 |

\* cited by examiner

PARTICULARLY STORAGE-STABLE AND THIXOTROPICALLY STABLE PROPHYLAXIS PASTE FOR PROFESSIONAL DENTAL USE

CROSS-REFERENCE TO RELATED APPLICATIONS

This application claims priority to German Patent Application No. 102013004088.4, filed Mar. 11, 2013, which is herein incorporated by reference in its entirety.

BACKGROUND OF THE INVENTION

The invention relates to dental care compositions for preventative dental hygiene which can generally be used by dentists on the patient in a cleaning cycle every several months, six months or a year. The compositions of these dental care compositions, which are also called prophylaxis pastes, differ from those of conventional toothpastes, which are generally used twice daily in the oral cavity by everyone without professional assistance.

The invention further relates to kits comprising the prophylaxis pastes according to the invention, to processes for producing the prophylaxis pastes, and to the use of the compositions according to the invention for producing the prophylaxis pastes.

Whereas toothpastes serve to remove food residues and give the consumer a refreshing mouth feel, the prophylaxis pastes serve for the polishing of teeth, the prevention of plaque formation, caries and gingivitis or for scale treatment, the removal of tooth stain discolorations and deposits which stubbornly adhere to the teeth, and also for preventing the development of sensitive teeth. Further indications relate to the cleaning and polishing of fillings, the polishing of the tooth surfaces prior to bleaching or following the removal of orthodontic devices in the course of professional tooth cleaning, and also the removal of residues of temporary luting material prior to the definitive bonding in place.

Pellicles, which settle as thin films on the tooth surfaces after cleaning the teeth and are formed from proteins in saliva, permit the adhesion of certain bacteria and the formation of biofilms. Plaque is formed on these films. Expert polishing using an appropriate prophylaxis paste suppresses biofilm growth, destroys the film and ensures that a rapid, new biofilm formation is temporarily suppressed on the polished, smooth tooth surface. However, it has to be ensured that, on the one hand, the cleaning and polishing effect of the paste has been optimally developed and, on the other hand, an abrasion which is harmful to health and damage to the tooth surfaces are minimized.

Prophylaxis pastes, which are applied by the dentist, are thus an important supplement to daily tooth cleaning. The additional dental treatment aims to assist dental care such that caries are reduced and further therapeutic measures become superfluous.

Prophylaxis pastes generally consist of three different pastes subdivided according to degrees of hardness. In dental practice, when carrying out the prophylaxis process, the tooth surface can be treated firstly with the hard paste, then with the medium-hard paste and finally with the soft paste. In the first operation, the tooth surface is roughened using the hard paste. The fluoride component in the paste is introduced into the rough tooth surfaces. The medium-hard and soft paste then polishes the coarse unevennesses on the teeth flat.

Alternatively, the pastes of differing hardness, which correspond to different cleaning intensities, can also be applied individually to the patient. It is then possible to individually deal with an individual patient situation here depending on the degree of dental contamination. However, in these cases too, after using a paste with a higher cleaning intensity, a final treatment with a soft paste should be carried out.

Prophylaxis pastes are known from the prior art.

US 2011/0059420 A1 describes a dental prophylaxis paste which has excellent flow properties during production, good usability on the patient and remineralizing properties. The paste comprises at least one water-soluble calcium salt, a water-soluble phosphate salt, a water-soluble fluoride compound, a silicate matrix, water and a humectant.

WO 2009/140577 A1 details oral compositions, where amorphous silicas with average particle sizes of 5 µm to 20 µm and an Einlehner hardness of 4 to 11 are used as cleaning agents.

EP 1 278 506 B1 discloses compositions of prophylaxis pastes which can be prepared using an abrasive substance of borosilicate glass of a specific composition having particle sizes of less than 200 µm and an average diameter of less than 50 µm.

U.S. Pat. No. 6,280,707 B1 discloses dental prophylaxis pastes with antimicrobial properties. The pastes comprise triclosan as antimicrobial active ingredient.

US 2002/0098156 A1 describes compositions of prophylaxis pastes in which roxite particles with average sizes of less than 5 µm are used as abrasives. Roxite is a polishing powder based on zirconium oxide that is preferably used in sizes of less than 1.3 µm.

EP 1 938 786 B1 discloses prophylaxis pastes which have expanded perlite with an average particle size of about 20 µm to about 70 µm and suspended particles as the sole cleaning and polishing body. The compositions comprise the perlite with a Darcy value in the range from about 0.1 to about 3 in amounts of from 40 to 55% by weight, about 5% by weight or less of a surfactant and more than 10% by weight of water.

DE 692 04 942 T2 claims a prophylaxis paste which comprises, as the sole, combined cleaning and polishing body, a finely divided rock with sharp-edged particles which disintegrates under application conditions into smaller, likewise sharp-edged particles and furthermore comprises 1,2-propanediol and a wetting agent, where the paste is virtually anhydrous. The finely divided rock used is perlite.

U.S. Pat. No. 7,332,150 B2 protects prophylaxis pastes which have cleaning bodies made of borosilicate glass with planar bodies in sizes of from 45 to 300 µm and a thickness of ca. 4 µm, where the small glass plates, upon exerting pressure, are aligned in parallel to the oral surface and their abrasive effect is thus reduced.

U.S. Pat. No. 6,280,707 B1 describes prophylaxis pastes consisting of triclosan as antibacterial additive, water, a humectant and a polishing body which is selected from the group consisting of pumice and clay, and also mixtures of pumice and clay.

DE 602 10 674 T2 indicates a surface treatment process for abrading a tooth surface coating in which an erasing agent is used which comprises a large number of particles, where the particles include a precipitate or agglomerate of calcium carbonate, where the process involves the step of contacting the surface with the erasing agent such that at least some of the particles roll along at least a section of the surface, where an angle of incidence of the particles and of the surface is between 0° and 60°, where the particles are generally round and have an irregular surface configuration, in order to carry out a rolling movement along the surface such that the particles rub on the coating and absorb it and where the erasing agent is essentially nonaqueous and where the particles have an average maximum diameter of between 30 and 1000 μm. The use of this process is provided inter alia for removing plaque and for the general cleaning and polishing of teeth and prostheses.

US 2011/0008270 relates to a water-soluble composition as prophylaxis paste, comprising a water-miscible liquid and at least 10% by weight of water-soluble particles which are selected from the group consisting of organic acids and salts thereof, amino acids and salts thereof, monosaccharides, disaccharides and mixtures of these components, where the composition is essentially free from water and the % s by weight refer to the total composition.

WO 2005/027863 is aimed at a mouth and dental care composition as polishing or cleaning agent, comprising a composite material comprising sparingly water-soluble calcium salts in the form of nanoparticulate primary particles with a length of 5 to 150 nm and a cross section of 2 to 50 nm and protein components selected from proteins, protein hydrolyzates and protein hydrolyzate derivatives and 0.1 to 9% by weight of a cleaning agent, based on the total weight of the composition.

WO 2010/009133 A2 describes a dental prophylaxis composition, during the application of which the dental surface is said to have no mechanical abrasion and where the nonabrasive polish comprises chlorine dioxide.

US 2010/0135925 A1 indicates prophylaxis pastes with cleaning bodies based on quartz glass. The quartz glass is an amorphous silica of high purity and has an average particle size of at least 7 μm. The compositions are said to produce PCR (pellicle cleaning ratio) values of at least 100.

DE 600 35 344 T2 discloses an antisensitivity dental mass which can also be used in a prophylaxis paste for polishing teeth or for treating sensitive teeth or for preventing the development of sensitive teeth following scale treatment, root cleaning and/or smoothing or stain removal by the dentist or hygienist.

EP 0 268 763 describes a prophylaxis paste which comprises, as cleaning body, a mixture consisting of a perlite and a synthetically produced precipitated silica, where the precipitated silica is obtained by homogeneously mixing together the precipitated silicas obtained in the usual manner by the precipitation route and of differing particle size and particle density in the suspension phase, and processing the mixtures in the usual manner by filtration, washing, drying and grinding.

EP 1 051 962 B1 claims a prophylaxis paste which has disc-like, plane or curved particles of a rock, in particular of perlite, as the main constituent of the cleaning body and a fraction of 20-80% by weight of polyether, cleaning bodies and polyether together constitute at least 30% by weight of the dental care composition and 0-20% by weight of emulsifier are present, where at least the polyether fraction serves for establishing the flow properties.

EP 2 286 786 A1 proposes a dental care composition for remineralizing teeth, having an active ingredient complex of hydroxylapatite and fluoride, where the active ingredient complex moreover has xylitol for allegedly increasing the remineralizing effect by the fluoride.

The majority of the prior art in connection with dental prophylaxis pastes is directed to the important problem of providing a cleaning body which cleans and polishes the teeth as thoroughly as possible and in so doing causes as little harmful abrasion as possible on the natural hard tooth substance.

A measure of the abrasion of hard tooth substance after using a cleaning and polishing paste on the teeth is the so-called RDA value (relative dentine abrasion).

The RDA values here were measured in accordance with DIN EN ISO 11609 (dental cleaning composition, requirement, test method and requirements). In this measurement method, teeth are radioactively irradiated and then brushed using the pastes and using a reference composition based on silica. Finally, the remaining radioactivity is measured and the samples are compared with the reference samples. The RDA values given here are averages from 6 sample measurements. The deviations are given by the variation coefficient (VC), a value which is obtained from the quotient of the standard deviation and the average, multiplied by 100.

SUMMARY OF THE INVENTION

It is an object of the present invention to indicate dental prophylaxis paste compositions which not only thoroughly clean and polish the teeth of the patient, but in particular also have particularly long storage stabilities and are particularly easy to use, where easy-to-use polishing pastes should have a thixotropically stable consistency.

DETAILED DESCRIPTION OF THE INVENTION

The use of the pastes by the dentist takes place for example by squeezing the pastes from tubes onto a receiver, from which the paste is taken up by a rotating application instrument with suitable cleaning and polishing attachments (cups, brushes). The rotating instrument attachments thus provided with the pastes are then placed onto the tooth surfaces to be treated, where application of the pastes takes place.

A particularly simple application is evident in a first step from the fact that the pastes can firstly be squeezed out easily, for example from the tubes, but secondly are immediately present in a stable form after being squeezed out, in order to be able to be taken up directly with the application instruments. Here, it is particularly important that the paste does not draw threads when being taken up from the receiver to the applicator. In this stage of the application, the nature of the paste must be such that its cohesive forces are as low as possible and no stickiness arises. In a second step, the stable paste present on the applicator is placed onto the tooth surfaces to be treated, and rotation of the applicator is started. In this stage, the formerly stable paste loses its solidity as a result of the action of shear forces, it begins to flow, builds up high forces of adhesion and now wets the surfaces of the teeth to be treated completely.

The term "thixotropically stable" is thus understood as meaning that the paste does not per se run, it can be readily taken up with the application tools (cups, brushes) and used in the oral cavity. The pastes only become softer when a shear force as a result of rotating instruments acts upon them during application. However, they also do not run in this situation since they very rapidly revert to the stable state again as soon as rotation subsides or stops.

These properties additionally also prevent a splashing of the pastes during paste application.

An exact measure of the thixotropic stability of the pastes is the value of the so-called "spreadability".

Our own extensive studies have revealed that pastes with spreadability values higher than 26 mm are too soft and no longer meet the requirement profile of the property "thixotropically stable" in the sense used herein.

Pastes with lower spreadability values than 16 mm have proven to be too solid. These also no longer satisfy the requirement profile of the property "thixotropically stable" in the sense used herein.

Pastes which have a spreadability of from and including 16 mm up to and including 26 mm correspond to the requirements according to the invention placed on the consistency. They have proven to be "thixotropically stable" in the sense used herein and are therefore optimal for a prophylaxis paste for professional dental use.

The determination of this value is explained in more detail later in the text.

"Particularly storage-stable" is understood as meaning that the pastes according to the invention, in contrast to the pastes known in the prior art, still have no signs of sedimentation/separation even after storage at highly elevated temperatures of up to 50° C. and varying humidities (rH) between 10% and 75% and prolonged periods of up to 9 months.

Storing of prophylaxis paste compositions was studied at 23° C. and 50% relative humidity (rH), at 40° C. and 75% relative humidity and at 50° C. and 10% relative humidity.

Results of the storage experiments as to stability using the example of a prophylaxis paste with coarse polishing bodies are given below in the experimental section.

Our own extensive studies have revealed that a good measure for predicting the stabilities after natural aging of the pastes is the value of the so-called centrifugal stability.

If, following this method, there are signs of sedimentations and/or separations in the investigated pastes upon visual inspection, the test is classed as "not passed", since the homogeneity of the phase is disturbed. If, after the centrifugation, a homogeneous paste is present which has no signs of any kind of separation and/or sedimentation, then the test is passed and the paste is in accordance with the invention or "in order" (OK). Pastes which pass this test will likewise remain stable following natural storage at elevated temperatures and the corresponding humidities even after aging.

The determination of this value is explained in more detail later in the text.

Surprisingly, it has been found that particularly storage-stable and thixotropically stable dental prophylaxis pastes, which are moreover very easy to use and thoroughly clean and polish the teeth of the patient and cause little abrasion of natural tooth substance can be attained by a paste composition which comprises a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8.

Such prophylaxis pastes are characterized in that they are particularly storage-stable, measured according to the method for determining the centrifugal stability, and are thixotropically stable, measured according to the method for determining the spreadability.

These special properties of the prophylaxis pastes can possibly be attributed to synergistic effects between the abrasive substances calcium phosphate and pumice, and also to the use of one or more amphoteric surfactants, the buffer system and the base component. The effect of the synergistic mixture on the stability and the rheological behavior of the paste is possibly further supported through the use of fumed silicas and further binders.

Prophylaxis pastes according to the invention thus have a so-called matrix element in the form of a base component consisting of water and the humectant. All of the components that are soluble in this element, such as the buffer components, surfactant, optionally cellulose derivatives, and additives, for example sodium fluoride, and stabilizers are then dissolved in succession therein and stirred in a kneading pot.

The insoluble components, such as abrasives, pigments, and aerosils are then added to the mixture and processed in a kneader to give a homogeneous mass.

Finally, the paste composition is degassed in vacuo and discharged into tubes, pots or cans.

Specifically, prophylaxis pastes according to the invention can preferably comprise the following components:

Water

Prophylaxis pastes according to the invention are aqueous compositions. The water is preferably prepared, i.e. demineralized, distilled or purified in another way. The amount of water used is 15 to 55% by weight, preferably 20 to 45% by weight and most preferably 23 to 35% by weight, the percentages by weight referring to the total amount of the prophylaxis paste composition.

Humectants

Humectants prevent the pastes from drying out and help to co-regulate the consistency of the pastes and to keep them stable. They also help create (like the surfactants) a suspension.

As a rule, the toxicologically acceptable polyols such as sorbitol, xylitol, glycerol, mannitol, 1,2-propylene glycol, and mixtures of these compounds are used. Although xylitol is also a sweetener, within the context of this invention, this compound is viewed as belonging to the humectants. Polyethylene or polypropylene glycols with average molecular weights of from 200 to 2000 g/mol are also suitable.

According to the invention, preference is given to the combination of glycerol, sorbitol and xylitol.

Depending on the product type, the total composition of the prophylaxis paste comprises the humectant or the mixture of humectants in an amount of from 10 to 60% by weight, preferably from 17 to 50% by weight and most preferably from 25 to 42% by weight. The ratio of humectant to water can be 1:3 to 3:1.

Thickeners (Component for Controlling the Rheology)

Binders and thickeners act as consistency regulators and control the viscosity and consistency of the pastes. In cooperation with the buffer system, the combination and amount of the humectant and the ratio thereof to the amount of water and type and amount of wetting agent, they prevent separation between the liquid and solid phases. In general, for example natural and/or synthetic water-soluble polymers such as alginates, starch and starch ethers, cellulose ethers such as e.g. carboxymethylcellulose, hydroxyethylcellulose, hydroxypropylcellu lose, methylhydroxy-propylcellulose, isopropylcellulose, methylcellulose, and mixtures of these derivatives, agar agar, xanthan, pectins, etc. are used.

Further suitable agents are water-soluble carboxyvinyl polymers, polyvinyl alcohols, polyvinyl pyrrolidones, polyvinyl acetates, polyvinylpyrrolidone-vinyl acetate copolymers, poly(meth)acrylates and poly(meth)acrylic acids, crosslinked poly(meth)acrylates, crosslinked poly(meth)acrylic acids, where the term (meth)acrylates includes both the acrylates and the methacrylates, polyalkylene oxides, polyvinyl alkyl ethers modified with maleic acid, etc.

It is likewise possible to use fumed silicas with a thickening action (which do not belong to the silica polishes). These silicas are preferably organically surface-modified.

According to the invention, preference is given to using fumed silicas and cellulose derivatives.

The amounts of thickeners used in the compositions according to the invention are 0.1 to 7% by weight, preferably 0.1 to 5% by weight and particularly preferably 0.1 to 4% by weight.

Surfactants

Surfactants are added as surface-active wetting agents to the compositions in order to improve the compatibility of the components with one another and to encourage the incorporation of water-insoluble substances, to increase the stability of the pastes and to ensure that the pastes are distributed rapidly and completely during use at the application site, i.e. on the tooth surfaces to be treated, and can thus also reach areas that are difficult to access, for example interdental spaces, so that the effect of the cleaners and of the dental care agents added to the pastes can also develop there. Surfactants assist for example the anticaries effect of fluorides.

According to the invention, the prophylaxis composition is based on the exclusive use of one or more amphoteric surfactants. Within the context of this invention, the term "amphoteric surfactant" is understood as meaning zwitterionic surfactants which have both a negatively charged functional group and a positively charged functional group. Like all surfactants "amphoteric surfactants" have a polar and a nonpolar moiety in their molecular structure. The surface-active compounds generally have an alkyl group as nonpolar moiety and at least one quaternary ammonium, phosphonium or sulfonium group and at least one carboxylate, sulfonate, sulfate, phosphate or phosphonate group as polar moiety. The aliphatic group here can be linear or branched, it usually carrying between 8 to 18 carbon atoms.

Surfactants that are particularly suitable for a prophylaxis paste according to the invention are the so-called betaines, such as the N-alkyl-N,N-dimethylammonium glycinates, for example trimethylammonium glycinate, cocoalkyldimethylammonium glycinate, N-acylaminopropyl-N,N-dimethylammonium glycinate or N-acylaminopropyl-N,N-dimethylammonium glycinate.

For the use in a prophylaxis paste according to the invention, particular preference is given to the fatty acid derivative known under the name Cocoamidopropyl Betaine, which is commercially available under the name "Tego Betain BL 215".

Of most particular preference for the use in a prophylaxis paste according to the invention is 2-[(3-dodecanamidopropyl)dimethylamino]acetate. Further suitable betaines for use in a composition according to the invention can be found in EP 2 198 836 A1.

The amounts of the wetting agent(s) used in the compositions according to the invention are 0.05 to 2.6% by weight, preferably 0.1 to 2.0% by weight and particularly preferably 0.8 to 1.2% by weight.

Buffer Components

A buffer system based on sodium dihydrogen phosphate and disodium hydrogen phosphate is used according to the invention. The buffer system ensures that the pH of the pastes remains stably adjusted between pH=7 and pH=8.

Preferably, the ratio of the amounts of sodium dihydrogen phosphate and disodium hydrogen phosphate used in the compositions according to the invention is 2:1 to 1:2.

Cleaning and Polishing Bodies

Cleaning and polishing agents belong to the most important constituents of a prophylaxis paste. They deal with the mechanical removal of plaque and lead to the shining of the tooth surface with minimal scouring effect and as far as possible no damage to the dental enamel and the dentine. The abrasion behavior of the cleaning and polishing bodies is for the large part determined by their degrees of hardness, particle size distributions and surface properties. When selecting suitable cleaning and polishing bodies, those which have a minimal abrasive effect with a high cleaning performance and a high polishing effect are generally selected.

Cleaning and polishing bodies according to the invention are, for example, calcium phosphates, pumice, so-called silica polishes such as precipitated silicas, gel silicas and hydrogel silicas, also silicates such as aluminum silicates and/or zirconium silicates, mixed silicates such as sodium aluminum silicate of the composition $Na_{12}(AlO_2)_{12}(SiO_2)_{12} \times 7\ H_2O$, synthetic zeolites, aluminum oxides, aluminum hydroxides, such as bentonites, zeolites, kaolin, mica, diatomaceous earth, calcium carbonate, magnesium carbonate, trimagnesium phosphate, polycarbonates, silicon carbide, boron carbide, etc., microcrystalline wax or else composite resins or organic polymers such as melamine resins, phenol resins or urea-formaldehyde resins, etc. According to the invention, preference is given to using water-insoluble inorganic substances, the use of a combination of water-insoluble calcium phosphates being essential to the invention, such as for example the use of the dibasic dicalcium orthophosphate $CaHPO_4$, the monobasic monocalcium phosphate $Ca(H_2PO_4)_2$, the tribasic tricalcium phosphate $Ca_3(PO_4)_2$, the pentacalciumhydroxy triphosphate $(Ca_5(PO_4)_3OH)$, and their hydrates, also of apatite $Ca_{10}(PO_4)_6(OH,F,Cl,Br)_2$ or of $Ca_8H_2(PO_4)_6 \times 5\ H_2O$, where one or more compounds can be used and pumice.

The use according to the invention of a combination of hydroxylapatite and pumice is particularly preferred.

Of several pumice variants investigated, those which have proven to be most advantageous have a fraction of particle sizes of less than 45 μm, stated as sieve residue in %, between 50 and 90%, most particularly preferably between 70 and 80%.

The amount of cleaning and polishing bodies used in the overall composition is between 0.5 and 60% by weight and particularly preferably 30 to 36% by weight. Like the selection of the agents and their ratio with one another, this is also dependent on the type of paste.

As described above, dental prophylaxis pastes are generally supplied in three different polishing strengths: one soft, one medium-hard and one hard prophylaxis paste. In the soft polishing and cleaning paste, the ratio of the amount of the cleaning bodies of the compound based on calcium phosphate to pumice is in the range from 40:1 to 10:1 according to the invention.

Here, the RDA value, measured in accordance with DIN EN ISO 11609, should according to the invention be in a range from 5 to 50, preferably in a range from 8 to 30.

In the medium-hard prophylaxis paste, the ratio of the amount of the cleaning bodies of the compound based on calcium phosphate to pumice is according to the invention in a range from 7:1 up to and including 3:1.

Here, the RDA value, measured in accordance with DIN EN ISO 11609, should according to the invention preferably be between 70 and 150, preferably in a range from 100 to 145.

In the hard prophylaxis paste, the ratio of the amount of the cleaning bodies of the compound based on calcium phosphate to pumice is according to the invention in a range from 3:1 to 1:1.

Here, the RDA value, measured in accordance with DIN EN ISO 11609, should according to the invention be in a range from 160 to 250, preferably in a range from 170 to 220.

Additives

Finally, further customary auxiliaries for improving the stability, the sensory properties and other properties may be present in the prophylaxis pastes according to the invention. Such additives are:

pigments such as titanium dioxide or zinc oxide, dyes preservatives such as hydroxybenzoic acid methyl, ethyl or propyl ester, sodium sorbate or sodium benzoate, fluoridation agents such as sodium fluoride, amine fluorides, potassium fluoride, tin fluoride, sodium monofluorophosphate or zinc fluoride.

The amount of additives used in the overall composition is preferably between 0.001 and 5% by weight.

The use of further auxiliaries in the prophylaxis paste compositions according to the invention is not excluded by virtue of this listing.

Particularly preferred embodiments of prophylaxis pastes according to the invention for professional dental use comprise a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, and where the compound based on calcium phosphate is hydroxylapatite.

Further particularly preferred embodiments of prophylaxis pastes according to the invention for professional dental use comprise a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, and where the fraction of particle sizes of the pumice of less than 45 μm, stated as sieve residue in %, is between 50 and 90%.

Further particularly preferred embodiments of prophylaxis pastes according to the invention for professional dental use comprise a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, and where the weight ratio of the two buffer components sodium dihydrogen phosphate and disodium hydrogen phosphate with one another is 2:1 to 1:2.

Further particularly preferred embodiments of prophylaxis pastes according to the invention for professional dental use comprise a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, and where the component for controlling the rheology d.) is a combination of fumed silica and a cellulose derivative.

Likewise particularly preferred embodiments of prophylaxis pastes according to the invention for professional dental use comprise a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8 and where the compound based on calcium phosphate is hydroxylapatite, and where the fraction of particle sizes of the pumice of less than 45 µm, stated as sieve residue in %, is between 50 and 90%.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the compound based on calcium phosphate is hydroxylapatite.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, where the component for controlling the rheology d.) is a combination of fumed silica and a cellulose derivative, and the compound based on calcium phosphate is hydroxylapatite.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the fraction of particle sizes of the pumice of less than 45 µm, stated as sieve residue in %, is between 50 and 90%.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, and where the component for controlling the rheology d.) is a combination of fumed silica and a cellulose derivative, and where the fraction of particle sizes of the pumice of less than 45 µm, stated as sieve residue in %, is between 50 and 90%.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the component for controlling the rheology d.) is a combination of fumed silica and a cellulose derivative.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, where the fraction of particle sizes of the pumice of less than 45 µm, stated as sieve residue in %, is between 50 and 90%, and where the compound based on calcium phosphate is hydroxylapatite.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additional component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the component for controlling the rheology d.) is a combination of fumed silica and a cellulose derivative, and the compound based on calcium phosphate is hydroxylapatite.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2 and where the component for controlling the rheology d.) is a combination of fumed silica and a cellulose derivative, and where the fraction of particle sizes of the pumice of less than 45 µm, stated as sieve residue in %, is between 50 and 90%.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8
and where the component for controlling the rheology d.) is a combination of fumed silica and a cellulose derivative, and the compound based on calcium phosphate is hydroxylapatite, where the fraction of particle sizes of the pumice of less than 45 µm, stated as sieve residue in %, is between 50 and 90%.

Further particularly preferred embodiments of prophylaxis pastes according to the invention for professional dental use comprise
a.) a base component comprising water and humectant,
b.) a cleaning body,
c.) a buffer component,
d.) a component for controlling the rheology,
e.) an additive component, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s),
where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the component for controlling the rheology d.) is a combination of fumed silica and a cellulose derivative, and the compound based on calcium phosphate is hydroxylapatite, where the fraction of particle sizes of the pumice of less than 45 µm, stated as sieve residue in %, is between 50 and 90%.

Likewise particularly preferred embodiments of prophylaxis pastes according to the invention for professional dental use comprise
a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the compound based on calcium phosphate is hydroxylapatite.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the weight ratio of the two buffer components sodium dihydrogen phosphate and disodium hydrogen phosphate with one another is 2:1 to 1:2.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the fraction of particle sizes of the pumice of less than 45 μm, stated as sieve residue in %, is between 50 and 90%.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the component for controlling the rheology d.) is a combination of fumed silica and a cellulose derivative.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent, f.) has exclusively one or more amphoteric surfactant(s) in an amount in the range from 0.05 to 2.6% by weight, preferably in the range from 0.1 to 2.0% by weight, where all of the % s by weight refer to the total mass of the prophylaxis paste and where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the compound based on calcium phosphate is hydroxylapatite.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the compound based on calcium phosphate is hydroxylapatite and where the fraction of particle sizes of the pumice of less than 45 µm, stated as sieve residue in %, is between 50 and 90%.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the component for controlling the rheology d.) is a combination of fumed silica and a cellulose derivative, and the compound based on calcium phosphate is hydroxylapatite.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the fraction of particle sizes of the pumice of less than 45 µm, stated as sieve residue in %, is between 50 and 90%.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents,
where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the component for controlling the rheology d.) is a combination of fumed silica and a cellulose derivative, and where the fraction of particle sizes of the pumice of less than 45 μm, stated as sieve residue in %, is between 50 and 90%.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, where the component for controlling the rheology d.) is a combination of fumed silica and a cellulose derivative.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, where the compound based on calcium phosphate is hydroxylapatite and where the fraction of particle sizes of the pumice of less than 45 μm, stated as sieve residue in %, is between 50 and 90%.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the component for controlling the rheology d.) is a combination of fumed silica and a cellulose derivative, and the compound based on calcium phosphate is hydroxylapatite, where the fraction of particle sizes of the pumice of less than 45 μm, stated as sieve residue in %, is between 50 and 90%.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the component for controlling the rheology d.) is a combination of fumed silica and a cellulose derivative, where the fraction of particle sizes of the pumice of less than 45 μm, stated as sieve residue in %, is between 50 and 90%.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another is 2:1 to 1:2, and where the component for controlling the rheology d.) is a combination of fumed silica and a cellulose derivative, and the compound based on calcium phosphate is hydroxylapatite.

Furthermore particularly preferred embodiments of prophylaxis pastes according to the invention for professional dental use comprise a.) a base component comprising water in the range from 15 to 55% by weight, preferably in the range from 20 to 45% by weight, and humectant in the range from 10 to 60% by weight, preferably in the range from 17 to 50% by weight,
b.) a cleaning body in the range from 0.5 to 60% by weight,
c.) a buffer component,
d.) a component for controlling the rheology in the range from 0.1 to 7% by weight, preferably in the range from 0.1 to 5% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.05 to 2.6% by weight, preferably in the range from 0.1 to 2.0% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the weight ratio of the two buffer components sodium dihydrogen phosphate and disodium hydrogen phosphate with one another in 2:1 to 1:2, and where the component for controlling the rheology d.) is a combination of fumed silica and a cellulose derivative, and the compound based on calcium phosphate is hydroxylapatite, where the fraction of particle sizes of the pumice of less than 45 μm, stated as sieve residue in %, is between 50 and 90%.

Most particularly preferred embodiments of prophylaxis pastes according to the invention for professional dental use comprise a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8.

Further most particularly preferred embodiments of prophylaxis pastes according to the invention for professional dental use comprise a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight,
where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the compound based on calcium phosphate is hydroxylapatite.

Further most particularly preferred embodiments of prophylaxis pastes according to the invention for professional dental use comprise a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight, where all of the %s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the fraction of particle sizes of the pumice of less than 45 μm, stated as sieve residue in %, is between 70 and 80%.

Further most particularly preferred embodiments of prophylaxis pastes according to the invention for professional dental use comprise
a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight,
where all of the %s by weight refer to the total mass of the prophylaxis paste, and where the buffer component c.) is based on hydrogen phosphate, and the weight ratio of the two buffer components sodium dihydrogen phosphate and disodium hydrogen phosphate with one another is 2:1 to 1:2, and where the buffer system keeps the pH of the prophylaxis paste, measured in a 10% suspension (w/w) of the paste in water against a pH electrode, between 7 and 8.

Further most particularly preferred embodiments of prophylaxis pastes according to the invention for professional dental use comprise
a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight,
where all of the %s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the component for controlling the rheology d.) is a combination of fumed silica and a cellulose derivative.

Further most particularly preferred embodiments of prophylaxis pastes according to the invention for professional dental use comprise
a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight,
where all of the %s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the compound based on calcium phosphate is hydroxylapatite and where the fraction of particle sizes of the pumice of less than 45 μm, stated as sieve residue in %, is between 70 and 80%.

Yet further most particularly preferred embodiments of prophylaxis pastes according to the invention for professional dental use comprise
a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight,
where all of the %s by weight refer to the total mass of the prophylaxis paste, and where the buffer component c.) is based on hydrogen phosphate, and the weight ratio of the two buffer components sodium dihydrogen phosphate and disodium hydrogen phosphate with one another is 2:1 to 1:2, and where the buffer system keeps the pH of the prophylaxis paste, measured in a 10% suspension (w/w) of the paste in water against a pH electrode, between 7 and 8, and where the compound based on calcium phosphate is hydroxylapatite.

Yet further most particularly preferred embodiments of prophylaxis pastes according to the invention for professional dental use comprise
a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight,
where all of the %s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, and where the component for controlling the rheology d.) is a combination of fumed silica and a cellulose derivative, where the fraction of particle sizes of the pumice of less than 45 μm, stated as sieve residue in %, is between 70 and 80%.

Yet further most particularly preferred embodiments of prophylaxis pastes according to the invention for professional dental use comprise a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight, where all of the %s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the component for controlling the rheology d.) is a combination of fumed silica and a cellulose derivative, and the compound based on calcium phosphate is hydroxylapatite.

Yet further most particularly preferred embodiments of prophylaxis pastes according to the invention for professional dental use comprise a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight, where all of the %s by weight refer to the total mass of the prophylaxis paste, and where the buffer component c.) is based on hydrogen phosphate, and the weight ratio of the two buffer components sodium dihydrogen phosphate and disodium hydrogen phosphate with one another is 2:1 to 1:2, and where the buffer system keeps the pH of the prophylaxis paste, measured in a 10% suspension (w/w) of the paste in water against a pH electrode, between 7 and 8, where the component for controlling the rheology d.) is a combination of fumed silica and a cellulose derivative.

Yet further most particularly preferred embodiments of prophylaxis pastes according to the invention for professional dental use comprise a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight, where all of the %s by weight refer to the total mass of the prophylaxis paste, and where the buffer component c.) is based on hydrogen phosphate, and the weight ratio of the two buffer components sodium dihydrogen phosphate and disodium hydrogen phosphate with one another is 2:1 to 1:2, and where the buffer system keeps the pH of the prophylaxis paste, measured in a 10% suspension (w/w) of the paste in water against a pH electrode, between 7 and 8, and where the fraction of particle sizes of the pumice of less than 45 μm, stated as sieve residue in %, is between 70 and 80%.

Yet further most particularly preferred embodiments of prophylaxis pastes according to the invention for professional dental use comprise a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent,
f.) has exclusively one or more amphoteric surfactant(s) in an amount in the range from 0.8 to 1.2% by weight, where all of the %s by weight refer to the total mass of the prophylaxis paste, and where the buffer component c.) is based on hydrogen phosphate, and the weight ratio of the two buffer components sodium dihydrogen phosphate and disodium hydrogen phosphate with one another is 2:1 to 1:2, and where the buffer system keeps the pH of the prophylaxis paste, measured in a 10% suspension (w/w) of the paste in water against a pH electrode, between 7 and 8, and where the compound based on calcium phosphate is hydroxylapatite, and where the fraction of particle sizes of the pumice of less than 45 μm, stated as sieve residue in %, is between 70 and 80%.

Yet further most particularly preferred embodiments of prophylaxis pastes according to the invention for professional dental use comprise a.) a base component comprising water in the range from 23 to 35% by weight, and humectant in the range from 25 to 42% by weight,
b.) a cleaning body in the range from 30 to 36% by weight,
c.) a buffer component,
d.) a component for controlling the rheology in the range from 0.1 to 4% by weight,
e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent, f.) has exclusively one or more amphoteric surfactant(s) in an amount in the range from 0.8 to 1.2% by weight, where all of the % s by weight refer to the total mass of the prophylaxis paste, and where the buffer component c.) is based on hydrogen phosphate and keeps the pH of the prophylaxis paste, measured in a 10% suspension (w/w) of the paste in water against a pH electrode, between 7 and 8, where the component for controlling the rheology d.) is a combination of fumed silica and a cellulose derivative, and the compound based on calcium phosphate is hydroxylapatite, and where the fraction of particle sizes of the pumice of less than 45 µm, stated as sieve residue in %, is between 70 and 80%.

Yet further most particularly preferred embodiments of prophylaxis pastes according to the invention for professional dental use comprise a.) a base component comprising water in the range from 23 to 35% by weight, and humectant in the range from 25 to 42% by weight, b.) a cleaning body in the range from 30 to 36% by weight, c.) a buffer component, d.) a component for controlling the rheology in the range from 0.1 to 4% by weight, e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent, f.) has exclusively one or more amphoteric surfactant(s) in an amount in the range from 0.8 to 1.2% by weight, where all of the % s by weight refer to the total mass of the prophylaxis paste, and where the buffer component c.) is based on hydrogen phosphate, and the weight ratio of the two buffer components sodium dihydrogen phosphate and disodium hydrogen phosphate with one another is 2:1 to 1:2, and where the buffer system keeps the pH of the prophylaxis paste, measured in a 10% suspension (w/w) of the paste in water against a pH electrode, between 7 and 8, where the component for controlling the rheology d.) is a combination of fumed silica and a cellulose derivative, and the compound based on calcium phosphate is hydroxylapatite.

Yet further most particularly preferred embodiments of prophylaxis pastes according to the invention for professional dental use comprise a.) a base component comprising water in the range from 23 to 35% by weight, and humectant in the range from 25 to 42% by weight, b.) a cleaning body in the range from 30 to 36% by weight, c.) a buffer component, d.) a component for controlling the rheology in the range from 0.1 to 4% by weight, e.) an additive component in the range from 0.001 to 5% by weight, where the additives are selected from list comprising stabilizers, dyes, pigments and fluoridation agents, where the prophylaxis paste comprises, as cleaning body b.), a compound based on calcium phosphate in combination with pumice and, as wetting agent, f.) has exclusively one or more amphoteric surfactant(s) in an amount in the range from 0.8 to 1.2% by weight, where all of the % s by weight refer to the total mass of the prophylaxis paste, and where the buffer component c.) is based on hydrogen phosphate and the weight ratio of the two buffer components sodium dihydrogen phosphate and disodium hydrogen phosphate with one another is 2:1 to 1:2, and where the buffer system keeps the pH of the prophylaxis paste, measured in a 10% suspension (w/w) of the paste in water against a pH electrode, between 7 and 8, where the component for controlling the rheology d.) is a combination of fumed silica and a cellulose derivative, and where the fraction of particle sizes of the pumice of less than 45 µm, stated as sieve residue in %, is between 70 and 80%.

Yet further most particularly preferred embodiments of prophylaxis pastes according to the invention for professional dental use comprise a.) a base component comprising water in the range from 23 to 35% by weight, and humectant in the range from 25 to 42% by weight, b.) a cleaning body in the range from 30 to 36% by weight, c.) a buffer component, d.) a component for controlling the rheology in the range from 0.1 to 4% by weight, e.) an additive component in the range from 0.001 to 5% by weight, where the additives are selected from a list comprising stabilizers, dyes, pigments and fluoridation agents, where the prophylaxis paste comprises, as cleaning body b.), a compound based on calcium phosphate in combination with pumice and, as wetting agent, f.) has exclusively one or more amphoteric surfactant(s) in an amount in the range from 0.8 to 1.2% by weight, where all of the % s by weight refer to the total mass of the prophylaxis paste, and where the buffer component c.) is based on hydrogen phosphate and the weight ratio of the two buffer components sodium dihydrogen phosphate and disodium hydrogen phosphate with one another is 2:1 to 1:2, and where the buffer system keeps the pH of the prophylaxis paste, measured in a 10% suspension (w/w) of the paste in water against a pH electrode, between 7 and 8, where the component for controlling the rheology d.) is a combination of fumed silica and a cellulose derivative, and the compound based on calcium phosphate is hydroxylapatite, and where the fraction of particle sizes of the pumice of less than 45 µm, stated as sieve residue in %, is between 70 and 80%.

The invention further relates to a kit, comprising tubes, pots or cans comprising soft and/or medium-hard and/or hard prophylaxis pastes each according to the invention as well as optionally cleaning and/or polishing cups and/or polishing brushes and/or fluoridation agents and/or bleaches and/or remineralizing agents and/or (fissure) sealers.

WORKING EXAMPLES OF THE INVENTION

Determination of the pH

To determine the pH, 2 g of substance are suspended in 20 ml of demineralized water. The pH is then measured against a pH electrode.

Determination of the Spreadability

The determination of the spreadability takes place in a climatically controlled room at a temperature of 23° C. and a relative humidity of 50% by means of a plastic glass plate arrangement. The dimensions of the plates are 60×60×5 mm for a plate weight of 25 g. During the determination, a syringe is used to place 0.5 ml of the respective paste onto the first plastic glass plate in the middle of the plate. The second plastic glass plate is then laid on parallel to the first and weighed down in the middle using a cylindrical iron punch (diameter: 33 mm, height: 13 mm) weighing 100 g for 10 minutes.

After the weighing down, the average of two diameters of the resulting sample cylinder is determined.

This method is a common process for determining the consistency when producing pastes.

Determination of the Centrifugal Stability

To assess the centrifugal stability, 3 g of the respective paste are weighed into a centrifuge glass that has a diameter of 15 mm and a length of 100 mm in a laboratory standard "EBA 20" centrifuge from Hettich. The paste is then centrifuged at 5000 rpm for 15 minutes. The temperature during the centrifugal run is 23° C.

RDA Values

The RDA values were ascertained as described above in accordance with DIN EN ISO 11609. The following values were obtained:

| Soft paste | RDA value 16 | (VC (%) 4.9) |
| Medium-hard paste | RDA value 127 | (VC (%) 10.1) |
| Hard paste | RDA value 195 | (VC (%) 2.4) |

The examples below serve to illustrate the present invention, but do not limit it in any way.

The preparation of the prophylaxis pastes in the examples shown below for various variations is as follows:

Into a matrix element consisting of water and the humectant are dissolved in succession all of the components that are soluble in this element, the buffer components, surfactant, optionally cellulose derivatives, and additives, for example sodium fluoride and stabilizers, and stirred in a kneading pot. The insoluble components such as abrasives, pigments, and aerosils are then added to the mixture and processed in a kneader to give a homogeneous mass.

Finally, the paste composition is degassed in vacuo and discharged into tubes, pots or cans.

Example 1

Using the example of various soft prophylaxis pastes, the aim is to illustrate the influence of different surfactant types on the physical properties. Here, identical paste formulations are used which differ only in the surfactant type (amphoteric, anionic, cationic).

| Ingredients | m % | m % | m % |
|---|---|---|---|
| Water | 27.00 | 27.00 | 27.00 |
| Glycerol (85%) | 10.36 | 10.36 | 10.36 |
| Sorbitol (70%) | 17.61 | 17.61 | 17.61 |
| Methylcellulose | 1.04 | 1.04 | 1.04 |
| Xylitol | 3.11 | 3.11 | 3.11 |
| Sodium fluoride | 0.15 | 0.15 | 0.15 |
| Stabilizers (paraben) | 0.21 | 0.21 | 0.21 |
| Sodium dihydrogen phosphate | 1.04 | 1.04 | 1.04 |
| Disodium hydrogen phosphate | 1.04 | 1.04 | 1.04 |
| Calcium phosphate | 33.12 | 33.12 | 33.12 |
| Pumice | 2.00 | 2.00 | 2.00 |
| Titanium dioxide | 1.04 | 1.04 | 1.04 |
| Fumed silica (<30 nm) | 1.24 | 1.24 | 1.24 |
| (1-Dodecyl)trimethylammonium chloride | 0.00 | 0.00 | 1.04 |
| Lauryl sulfate | 0.00 | 1.04 | 0.00 |
| Betaine | 1.04 | 0.00 | 0.00 |
| Total | 100.0 | 100.0 | 100.0 |
| pH | 7.34 | 7.33 | 7.27 |
| Centrifugal stability | OK | OK | not passed |
| Spreadability | 18.0 | 27 | 29 |
| Appearance | Good | Barely thixotropic | Inhomogeneous |

Surprisingly, it is found that the use of anionic or cationic surfactants leads to considerably different properties compared with the pastes according to the invention.

The prophylaxis paste formulated with an anionic surfactant is extremely soft and exhibits only a very weakly pronounced thixotropically stable behavior corresponding to the value of the spreadability. Additional experiments moreover showed that good wetting of the tooth surface cannot be achieved with this composition.

When using a cationic surfactant, a per se inhomogeneous, likewise very soft prophylaxis paste is obtained. In the centrifuge and during storage, sedimentation of the cleaning bodies very rapidly results. A successful dental prophylactic application is not possible with such a paste system. This is in contrast to the prophylaxis paste according to the invention with an amphoteric surfactant which is characterized by its thixotropically stable behavior with simultaneously good storage stability.

Example 2

Using the example of different hard prophylaxis pastes the aim is to explain what influence different percentage fractions of amphoteric surfactant have in prophylaxis pastes.

| Ingredients | m % | m % | m % | m % | m % |
|---|---|---|---|---|---|
| Water | 26.78 | 27.06 | 26.92 | 26.51 | 26.24 |
| Glycerol (85%) | 16.28 | 16.45 | 16.36 | 16.11 | 15.95 |
| Sorbitol (70%) | 12.36 | 12.49 | 12.43 | 12.24 | 12.11 |
| Methylcellulose | 1.03 | 1.04 | 1.04 | 1.02 | 1.01 |
| Xylitol | 5.15 | 5.20 | 5.18 | 5.10 | 5.05 |
| Sodium fluoride | 0.14 | 0.15 | 0.14 | 0.14 | 0.14 |
| Stabilizers (paraben) | 0.21 | 0.21 | 0.21 | 0.20 | 0.20 |
| Sodium dihydrogen phosphate | 1.03 | 1.04 | 1.04 | 1.02 | 1.01 |
| Disodium hydrogen phosphate | 1.03 | 1.04 | 1.04 | 1.02 | 1.01 |
| Fumed silica (<30 nm) | 1.99 | 2.01 | 2.00 | 1.97 | 1.95 |
| Titanium dioxide | 1.03 | 1.04 | 1.04 | 1.02 | 1.01 |
| Calcium phosphate | 16.48 | 16.65 | 16.57 | 16.31 | 16.15 |
| Pumice | 15.45 | 15.62 | 15.51 | 15.30 | 15.14 |
| Betaine | 1.04 | 0.00 | 0.52 | 2.04 | 3.03 |
| Total | 100.0 | 100.0 | 100.0 | 100.0 | 100.0 |
| pH | 7.22 | 7.28 | 7.28 | 7.24 | 7.23 |
| Centrifugal stability | OK | Not passed | OK | OK | Not passed |
| Spreadability | 20 | 27 | 20.5 | 22 | 29.5 |
| Appearance | Good | Very soft & separation | Good | Good | Very soft & separation |

It is found that an excessively high or low fraction of amphoteric surfactant leads to a very soft consistency, which is reflected in the values for the spreadability. Additional experiments showed, moreover, that good wetting of tooth surfaces cannot be achieved with these compositions.

In the centrifuge and during storage, sedimentation of the cleaning bodies very rapidly results. Successful dental prophylactic application is not possible with such a paste system.

Example 3

Using the example of different prophylaxis pastes (soft, medium-hard, hard), the aim is to illustrate the influence of the pH on the properties of the pastes. To vary the pH in the pastes, the disodium hydrogen phosphate is kept constant and the content of acidic sodium dihydrogen phosphate is varied.

Experimental Series 1: Soft Pastes

| Ingredients | m % | m % | m % | m % | m % |
|---|---|---|---|---|---|
| Water | 27.00 | 27.31 | 27.15 | 26.71 | 26.41 |
| Glycerol (85%) | 10.36 | 10.47 | 10.41 | 10.25 | 10.15 |
| Sorbitol (70%) | 17.61 | 17.79 | 17.70 | 17.43 | 17.25 |
| Methylcellulose | 1.04 | 1.05 | 1.04 | 1.03 | 1.01 |
| Xylitol | 3.11 | 3.14 | 3.12 | 3.08 | 3.04 |
| Sodium fluoride | 0.15 | 0.15 | 0.15 | 0.14 | 0.14 |
| Stabilizers (paraben) | 0.21 | 0.21 | 0.21 | 0.21 | 0.20 |
| Sodium dihydrogen phosphate | 1.04 | 0.00 | 0.53 | 2.05 | 3.04 |
| Disodium hydrogen phosphate | 1.04 | 1.03 | 1.04 | 1.03 | 1.01 |
| Calcium phosphate | 33.12 | 33.49 | 33.32 | 32.78 | 32.47 |
| Pumice | 2.00 | 2.00 | 2.00 | 2.00 | 2.00 |
| Titanium dioxide | 1.04 | 1.05 | 1.04 | 1.03 | 1.01 |
| Fumed silica (<30 nm) | 1.24 | 1.26 | 1.25 | 1.23 | 1.22 |
| Betaine | 1.04 | 1.05 | 1.04 | 1.03 | 1.05 |
| Total | 100.0 | 100.0 | 100.0 | 100.0 | 100.0 |
| pH | 7.34 | 8.27 | 7.68 | 7.04 | 6.66 |
| Centrifugal stability | OK | Not passed | OK | OK | OK |
| Spreadability | 18.5 | 27 | 19.5 | 16 | 14 |
| Appearance | Good | Soft & creamy | Good | Good | very stable & dry |

Experimental Series 2: Medium-Hard Pastes

| Ingredients | m % | m % | m % | m % | m % |
|---|---|---|---|---|---|
| Water | 24.20 | 24.46 | 24.33 | 23.96 | 23.72 |
| Glycerol (85%) | 16.14 | 16.31 | 16.22 | 15.97 | 15.82 |
| Sorbitol (70%) | 6.05 | 6.11 | 6.08 | 5.99 | 5.93 |
| Methylcellulose | 1.01 | 1.02 | 1.01 | 1.00 | 0.99 |
| Xylitol | 14.12 | 14.27 | 14.19 | 13.98 | 13.84 |
| Sodium fluoride | 0.14 | 0.14 | 0.14 | 0.14 | 0.14 |
| Stabilizers (paraben) | 0.20 | 0.20 | 0.20 | 0.20 | 0.20 |
| Sodium dihydrogen phosphate | 1.01 | 0.00 | 0.51 | 2.00 | 2.97 |
| Disodium hydrogen phosphate | 1.01 | 1.02 | 1.03 | 1.00 | 0.99 |
| Fumed silica (<30 nm) | 1.84 | 1.85 | 1.84 | 1.82 | 1.80 |
| Titanium dioxide | 1.01 | 1.02 | 1.01 | 1.00 | 0.99 |
| Calcium phosphate | 24.22 | 24.50 | 24.35 | 23.95 | 23.70 |
| Pumice | 8.04 | 8.08 | 8.08 | 7.99 | 7.92 |
| Betaine | 1.01 | 1.02 | 1.01 | 1.00 | 0.99 |
| Total | 100.0 | 100.0 | 100.0 | 100.0 | 100.0 |
| pH | 7.28 | 8.2 | 7.64 | 7.03 | 6.60 |
| Centrifugal stability | OK | Not passed | OK | OK | OK |
| Spreadability | 19 | 27 | 21 | 16 | 14 |
| Appearance | Good | Soft & separation | Good | Good | Stable & dry |

Experimental Series 3: Hard Pastes

| Ingredients | m % | m % | m % | m % | m % |
|---|---|---|---|---|---|
| Water | 26.78 | 27.06 | 26.92 | 26.51 | 26.24 |
| Glycerol (85%) | 16.28 | 16.45 | 16.36 | 16.11 | 15.95 |
| Sorbitol (70%) | 12.36 | 12.49 | 12.43 | 12.24 | 12.11 |
| Methylcellulose | 1.03 | 1.04 | 1.04 | 1.02 | 1.01 |
| Xylitol | 5.15 | 5.20 | 5.18 | 5.10 | 5.05 |
| Sodium fluoride | 0.14 | 0.15 | 0.14 | 0.14 | 0.14 |
| Stabilizers (paraben) | 0.21 | 0.21 | 0.21 | 0.20 | 0.20 |
| Sodium dihydrogen phosphate | 1.03 | 0.00 | 0.52 | 2.04 | 3.03 |
| Disodium hydrogen phosphate | 1.03 | 1.04 | 1.04 | 1.02 | 1.01 |
| Fumed silica (<30 nm) | 1.99 | 2.01 | 2.00 | 1.97 | 1.95 |
| Titanium dioxide | 1.03 | 1.04 | 1.04 | 1.02 | 1.01 |
| Calcium phosphate | 16.48 | 16.65 | 16.57 | 16.31 | 16.15 |
| Pumice | 15.45 | 15.62 | 15.51 | 15.30 | 15.14 |
| Betaine | 1.04 | 1.04 | 1.04 | 1.02 | 1.01 |
| Total | 100.0 | 100.0 | 100.0 | 100.0 | 100.0 |
| pH | 7.26 | 8.39 | 7.67 | 7.04 | 6.65 |
| Centrifugal stability | OK | Not passed | OK | OK | OK |
| Spreadability | 21 | 27 | 22 | 16 | 13 |
| Appearance | Good | Soft & separation | Good | Good | Stable & dry |

The variation in the acidic monosodium dihydrogen phosphate leads to a considerable pH fluctuation in the various pastes.

It is found that in the basic range above pH=8 the consistency is very thin and the pastes separate very rapidly, whereas in the acidic range below pH=7 the pastes become very stable and dry. These pastes no longer correspond to the requirement profile according to the invention.

The experiments show that the optimum pH range for the pastes is between 7 and 8. Above this range, in more basic conditions, or below this range, in acidic conditions, the pastes no longer have the properties according to the invention. The optimum pH range can be established precisely by a combination of different amounts of monosodium dihydrogen phosphate and disodium dihydrogen phosphate.

Example 4

Using the example of a hard prophylaxis paste, the aim is to explain the influence of the temperature and humidity on the properties of a hard paste according to the invention over a period of 9 months. The paste was studied at 23° C., 50% rH, 40° C., 75% rH and 50° C., 10% rH.

Hard Paste Used:

| Ingredients | m % |
|---|---|
| Water | 26.78 |
| Glycerol (85%) | 16.28 |
| Sorbitol (70%) | 12.36 |
| Methylcellulose | 1.03 |
| Xylitol | 5.15 |
| Sodium fluoride | 0.14 |
| Stabilizers (paraben) | 0.21 |
| Sodium dihydrogen phosphate | 1.03 |
| Disodium hydrogen phosphate | 1.03 |
| Fumed silica (>30 nm) | 1.99 |
| Titanium dioxide | 1.03 |
| Calcium phosphate | 16.48 |
| Pumice | 15.45 |
| Betaine | 1.04 |
| Total | 100.0 |

| | | Start | 1 Mo | 2 Mo | 4 Mo | 6 Mo | 9 Mo |
|---|---|---|---|---|---|---|---|
| 23° C.; 50% RH | Centrifugal stability | OK | OK | OK | OK | OK | OK |
| | Spreadability [mm] | 20.5 | 20 | 21 | 20 | 20 | 20 |
| | pH | 7.38 | 7.24 | 7.4 | 7.4 | 7.47 | 7.47 |
| 40° C.; 75% | Centrifugal stability | OK | OK | OK | OK | OK | OK |

| | | | | | | |
|---|---|---|---|---|---|---|
| RH | Spreadability [mm] | 20.5 | 19 | 19 | 19 | 20 | 20 |
| | pH | 7.38 | 7.36 | 7.52 | 7.48 | 7.54 | 7.54 |
| 50° C.; 10% RH | Centrifugal stability | OK | OK | OK | OK | OK | OK |
| | Spreadability [mm] | 20.5 | 19 | 18 | 18 | 20 | 20 |
| | pH | 7.38 | 7.41 | 7.55 | 7.49 | 7.49 | 7.49 |

The experiment shows that the prophylaxis paste according to the invention still have no signs of sedimentation/separation even after storage at highly elevated temperatures of up to 50° C. and different humidities (RH) between 10% and 75% and for longer periods up to 9 months. The thixotropically stable properties according to the invention are also retained over the entire period. Prophylaxis pastes from the prior art do not have these properties.

The invention claimed is:

1. A prophylaxis paste for professional dental use, comprising
   a.) a base component comprising water and humectant,
   b.) a cleaning body,
   c.) a buffer component,
   d.) a component for controlling the rheology,
   e.) an additive component, wherein the additives are selected from the group consisting of stabilizers, dyes, pigments and fluoridation agents, and
   f.) a wetting agent consisting of one or more amphoteric surfactant(s),
   wherein the cleaning body comprises a calcium phosphate in combination with pumice;
   wherein the amphoteric surfactant is a betaine;
   wherein the calcium phosphate is selected from the group consisting of the dibasic dicalcium orthophosphate $CaHPO_4$, the monobasic monocalcium phosphate $Ca(H_2PO_4)_2$, the tribasic tricalcium phosphate $Ca_3(PO_4)_2$, the pentacalciumhydroxy triphosphate ($Ca_5(PO_4)_3OH$) (hydroxylapatite), and hydrates thereof, apatite $Ca_{10}(PO_4)_6(OH,F,Cl,Br)_2$, and $Ca_8H_2(PO_4)_6 \times 5H_2O$; and
   wherein the buffer component is a hydrogen buffer and keeps the pH of the prophylaxis paste, measured in a 10% suspension (w/w) of the paste in water against a pH electrode, between 7 and 8.

2. The prophylaxis paste for professional dental use according to claim 1, wherein the calcium phosphate is hydroxylapatite.

3. The prophylaxis paste for professional dental use according to claim 1, wherein between 50 and 90% of the pumice has a particle size of less than 45 µm, and wherein the percent pumice is sieve residue in %.

4. The prophylaxis paste for professional dental use according to claim 1, wherein the buffer component comprises sodium dihydrogen phosphate and disodium hydrogen phosphate in a weight ratio with one another of 2:1 to 1:2.

5. The prophylaxis paste for professional dental use according to claim 1, wherein the component for controlling the rheology d.) is a combination of fumed silica and a cellulose derivative.

6. The prophylaxis paste for professional dental use according to claim 1, wherein the paste comprises
   water in the range from 15 to 55% by weight, and humectant in the range from 10 to 60% by weight,
   a cleaning body in the range from 0.5 to 60% by weight,
   a component for controlling the rheology in the range from 0.1 to 7% by weight,
   an additive component in the range from 0.001 to 5% by weight,
   one or more amphoteric surfactant(s) in an amount in the range from 0.05 to 2.6% by weight,
   wherein all of the % s by weight refer to the total mass of the prophylaxis paste.

7. The prophylaxis paste for professional dental use according to claim 1, wherein the paste comprises
   water in the range from 23 to 35% by weight and humectant in the range from 25 to 42% by weight,
   a cleaning body in the range from 30 to 36% by weight,
   a component for controlling the rheology in the range from 0.1 to 4% by weight,
   an additive component in the range from 0.001 to 5% by weight,
   one or more amphoteric surfactant(s) in an amount in the range from 0.80 to 1.20% by weight,
   wherein all of the % s by weight refer to the total mass of the prophylaxis paste.

8. The prophylaxis paste for professional dental use according to claim 1, characterized in that it is storage-stable, measured according to the method for determining the centrifugal stability, wherein the determination of the centrifugal stability takes place using a laboratory standard centrifuge (EBA 20® from Hettich) and wherein 3 g of the respective paste are weighed into a centrifuge glass that has a diameter of 15 mm and a length of 100 mm and then centrifuged at 5000 rpm for 15 minutes, wherein the temperature during the centrifugal run is 23° C. and wherein, following this method, the investigated pastes are examined visually as to phase homogeneity, and is thixotropically stable, measured according to the method for determining the spreadability, wherein the determination of the spreadability takes place in a climatically controlled room at a temperature of 23° C. and a relative atmospheric humidity of 50% by means of a plastic glass plate arrangement, wherein the dimensions of the plates are 60×60×5 mm and wherein the plate weight is 25 g and wherein a syringe is used to place 0.5 ml of the respective paste onto the first plastic glass plate in the middle of the plate and wherein then the second plastic glass plate is laid on parallel to the first and weighed down in the middle using a cylindrical iron punch weighing 100 g and having a diameter of 33 mm and a height of 13 mm for 10 minutes, and wherein the value of the spreadability is determined as the average of two diameters of the resulting sample cylinder after the weighing down.

9. A kit, comprising tubes, pots or cans comprising one or more soft prophylaxis paste(s) according to claim 1, wherein the ratio of the cleaning bodies of the compound based on calcium phosphate to pumice is in a range from 40:1 to 10:1 and the RDA value of the soft paste(s), measured in accordance with DIN EN ISO 11609, is in the range from 5 to 50, and/or one or more medium-hard prophylaxis paste(s) according to claim 1, wherein the ratio of the cleaning bodies of the compound based on calcium phosphate to pumice is in a range from 7:1 up to and including 3:1 and the RDA value of the medium-hard paste(s), measured in accordance with DIN EN ISO 11609, is in the range from 70 to 150, and/or one or more hard prophylaxis paste(s) according to one of the preceding claims, wherein the ratio of the cleaning bodies of the compound based on calcium phosphate to pumice is in a range from 3:1 to 1:1 and the RDA value of the hard paste(s), measured in accordance with DIN EN ISO 11609, is in the range from 160 to 250.

10. A process for producing a prophylaxis paste according to claim 1 having the following steps:
   a.) providing the base component consisting of water and humectant,
   b.) successively dissolving all of the other constituents of the prophylaxis paste that are soluble in this component,
   c.) introducing the constituents that are insoluble in this mixture,
   d.) processing the mixture to give a homogeneous mass,
   e.) degassing the prophylaxis paste composition in vacuo, and
   f.) discharging the prophylaxis paste into tubes, pots or cans.

11. The prophylaxis paste for professional dental use according to claim 3, wherein between 70 and 80% of the pumice has a particle size of less than 45 μm, wherein the percent pumice sieve residue in %.

12. The prophylaxis paste for professional dental use according to claim 6, wherein the paste comprises
   water in the range from 20 to 45% by weight, and humectant in the range from 17 to 50% by weight,
   a component for controlling the rheology in the range from 0.1 to 5% by weight,
   one or more amphoteric surfactant(s) in an amount in the range from 0.1 to 2.0% by weight,
   wherein all of the % s by weight refer to the total mass of the prophylaxis paste.

13. The kit according to claim 9, wherein the RDA value of the soft paste(s) is in the range from 8 to 30, the RDA value of the medium-hard paste(s) is in the range from 100 to 145, and the RDA value of the hard paste(s) is in the range from 170 to 220.

14. The kit according to claim 9, wherein the kit further comprises a component selected from the group consisting of cleaning and/or polishing cups, polishing brushes, fluoridation agents, bleaches, remineralizing agents, (fissure) sealers, and combinations thereof.

15. A prophylaxis paste for professional dental use, comprising
   a.) a base component comprising water and humectant,
   b.) a cleaning body,
   c.) a buffer component,
   d.) a component for controlling the rheology,
   e.) an additive component, wherein the additives are selected from the group consisting of stabilizers, dyes, pigments and fluoridation agents, and
   f.) a wetting agent consisting of one or more amphoteric surfactant(s),
   wherein the cleaning body comprises a calcium phosphate in combination with pumice;
   wherein the calcium phosphate is selected from the group consisting of the dibasic dicalcium orthophosphate $CaHPO_4$, the monobasic monocalcium phosphate $Ca(H_2PO_4)_2$, the tribasic tricalcium phosphate $Ca_3(PO_4)_2$, the pentacalciumhydroxy triphosphate ($Ca_5(PO_4)_3OH$) (hydroxylapatite), and hydrates thereof, apatite $Ca_{10}(PO_4)_6(OH,F,Cl,Br)_2$, and $Ca_8H_2(PO_4)_6 \times 5H_2O$;
   wherein the buffer component is a hydrogen phosphate buffer and keeps the pH of the prophylaxis paste, measured in a 10% suspension (w/w) of the paste in water against a pH electrode, between 7 and 8; and
   wherein the prophylaxis paste is particularly storage-stable for up to 9 months.

* * * * *